United States Patent
Tang et al.

(10) Patent No.: US 11,731,098 B2
(45) Date of Patent: Aug. 22, 2023

(54) METHOD FOR EXTRACTING NERVE TISSUE-DERIVED EXOSOMES

(71) Applicant: NANTONG UNIVERSITY, Jiangsu (CN)

(72) Inventors: Xin Tang, Jiangsu (CN); Cheng Sun, Jiangsu (CN); Xiaokun Gu, Jiangsu (CN); Xiaosong Gu, Jiangsu (CN); Qianru He, Jiangsu (CN); Tianmei Qian, Jiangsu (CN); Wenfeng Su, Jiangsu (CN); Haoming Li, Jiangsu (CN)

(73) Assignee: NANTONG UNIVERSITY, Jiangsu (CN)

( * ) Notice: Subject to any disclaimer, the term of this patent is extended or adjusted under 35 U.S.C. 154(b) by 0 days.

(21) Appl. No.: 17/628,754

(22) PCT Filed: Jan. 15, 2021

(86) PCT No.: PCT/CN2021/072183
§ 371 (c)(1),
(2) Date: Jan. 20, 2022

(87) PCT Pub. No.: WO2022/134246
PCT Pub. Date: Jun. 30, 2022

(65) Prior Publication Data
US 2022/0395795 A1    Dec. 15, 2022

(30) Foreign Application Priority Data

Dec. 25, 2020   (CN) .......................... 202011574532.8

(51) Int. Cl.
*B01J 13/02* (2006.01)
*C07K 1/14* (2006.01)
*C07K 1/22* (2006.01)
*C12N 5/079* (2010.01)

(52) U.S. Cl.
CPC ................ *B01J 13/02* (2013.01); *C07K 1/14* (2013.01); *C12N 5/0618* (2013.01)

(58) Field of Classification Search
None
See application file for complete search history.

(56) References Cited

U.S. PATENT DOCUMENTS

2010/0003197 A1* 1/2010 Bikram ............... A61K 49/186
977/773
2018/0340945 A1* 11/2018 Mitsuhashi ............ A61P 25/00

FOREIGN PATENT DOCUMENTS

| CN | 106366196 A | 2/2017 |
|---|---|---|
| CN | 107648667 A | 2/2018 |
| CN | 109576210 A | 4/2019 |
| CN | 110295142 A | 10/2019 |
| CN | 110308280 A | 10/2019 |
| CN | 110432320 A | 11/2019 |
| CN | 112111042 A | 12/2020 |
| WO | 2016123556 A1 | 8/2016 |

OTHER PUBLICATIONS

Hao, Xinxin et al.; "Stem cell-mediated delivery of nanogels loaded with ultrasmall iron oxide nanoparticles for enhanced tumor MR imaging"; Nanoscale; 2012 vol. 00; pp. 1-8.
Greening, David W. et al.; "A protocol for exosome isolation and characterization:evaluation of ultracentrifugation, density-gradient separation,and immunoaffinity capture methods"; Methods and Protocols, Methods in Molecular Biology, vol. 1295; 2015; pp. 179-209.

* cited by examiner

*Primary Examiner* — Daniel E Kolker
*Assistant Examiner* — James L Rogers
(74) *Attorney, Agent, or Firm* — NKL Law; Allen Xue

(57) ABSTRACT

Ag—Fe3O4 immunomagnetic microsphere contains poly-D-lysine modified on the surface and S100β and/or MBP antibody linked by an amide bond. The Ag—Fe3O4 immunomagnetic microsphere can specifically capturing peripheral nerve tissue-derived exosomes. When the microsphere is used to extract nerve tissue-derived exosomes, the extraction yield of exosomes per unit volume of nerve tissue is high, and the nerve specificity is strong.

9 Claims, 2 Drawing Sheets

METHOD FOR EXTRACTING NERVE TISSUE-DERIVED EXOSOMES

BACKGROUND

Technical Field

The present invention relates to the field of biotechnologies, and in particular to an Ag—$Fe_3O_4$ immunomagnetic microsphere and a method for extracting nerve tissue-derived exosomes using the microsphere.

Related Art

Exosomes are membrane-bound nanovesicles with a diameter of 30-150 nm and a phospholipid bilayer structure on the surface that are actively secreted out of a cell by endosomal membrane budding. Due to the secretion and release from different types of cells, exosomes usually carry cell-specific components such as various proteins, mRNAs and miRNAs. They participate in regulating a variety of signaling pathways by transmitting signal molecules, and can directly fuse with cells by endocytosis and other means. Recent studies have found that in a normal physiological environment, the content in an exosome will show a tissue and cell specificity due to a different tissue and cell source, and in a pathological state, the content in an exosome will vary with the change in the extracellular environment. Therefore, the detection and use of exosomes has received more and more attention in clinic. For example, in clinical molecular diagnosis, exosomes can be used as biomarker molecules. In addition, by means of molecular biology techniques such as genetic modification, exosomes can also be used as drug carriers for drug delivery to achieve targeted therapy in vivo. Exosomes are specifically tropic to target cells or tissues, easily pass through biological barriers, and have good biocompatibility and low immunogenicity, thus having broad prospect of application in clinical drug delivery and targeted therapy.

Schwann cells play an important role in peripheral nerve regeneration and are one of the most important and commonly used seed cells in neural tissue engineering. S100β protein is expressed and secreted by neuroectoderm cells. It is a soluble acidic calcium-binding protein belonging to the troponin C family, and is the most active member of the S100 family in the nervous system, which is mainly located in astrocytes and oligodendrocytes in the central nervous system and Schwann cells in the peripheral nervous system. As a specific protein in the nervous system, S100β participates in the formation and maintenance of the cell membrane surface composed of phospholipids, affects the depolymerization of microtubules and microfilaments, participates in regulating the phosphorylation of protein kinase C and calmodulin and the synthesis of RNA, has the effect of nurturing nerves. and promotes the growth of nerves and the repair of damage.

Myelin sheath is a myelin membrane formed by neuroglial cells wrapping nerve axons. The main physiological function is to ensure the smooth passage of sodium ions. The electrical signals from neurons achieve saltatory conduction at the nodes of Ranvier, increasing the conduction rate and energy efficiency of axon signals and providing insulation for preventing the spread of nerve impulses between nodes of Ranvier. Myelin basic protein (MBP) accounts for 30% of the total myelin protein and is located on the serosal surface of myelin. It is a basic membrane protein unique to myelin and contains a variety of basic amino acids. MBP is mainly synthesized and secreted by oligodendrocytes in the central nervous system and Schwann cells in the peripheral nervous system, and plays a vital role in the differentiation of nerve cells, myelination, and the maintenance of the stability of the nervous system.

At present, the main research methods for obtaining exosomes are to extract exosomes secreted by specific cells from the culture of the specific cells and to collect exosomes from body fluids. However, the environment of in-vitro culture is not the same as the environment in the body. The exosomes secreted by these cells cannot accurately mimic the exosomes derived from the environment in the body. The exosomes collected from body fluids are usually a mixture of exosomes from various tissues and organs. These exosomes derived from different tissue and cells have tissue and cell specificity. Ensuring the tissue and cell specificity of exosomes is of great significance for further research on the occurrence and development of the diseases associated with the specific tissue and organ.

Existing commonly used methods for separation and extraction of exosomes mainly include ultracentrifugation, density gradient centrifugation, membrane filtration, and size exclusion chromatography. However, most of them have low recovery rates, and are time-consuming, labor-intensive and expensive, and the exosomes are easy to rupture to produce a large amount of proteins and suffer from lipid contamination.

SUMMARY

The present invention constructs an Ag—$Fe_3O_4$ magnetic microsphere linked with S100β and/or MBP antibody and modified with poly-D-lysine, which can specifically capture exosomes derived from peripheral nerve tissue. When the microsphere is used to extract nerve tissue-derived exosomes, the extraction yield of exosomes per unit volume of nerve tissue is high, and the nerve specificity is strong. Therefore, the present invention provides a new method for clinical treatment of peripheral nerve injury.

The specific technical solutions provided in the present invention are as follows:

An Ag—$Fe_3O_4$ immunomagnetic microsphere comprises poly-D-lysine modified on the surface and S100β and/or MBP antibody linked by an amide bond.

The Ag—$Fe_3O_4$ immunomagnetic microsphere of the present invention can be prepared through a process comprising:

(1) dissolving a $Fe^{2+}$ and a $Fe^{3+}$ metal salt in an aqueous triethanolamine solution, heating (preferably at 75° C.), adding an aqueous $Ag^+$ (such as silver nitrate) solution under an inert gas atmosphere, magnetically stirring, dispersing, and washing the Ag—$Fe_3O_4$ microsphere until neutral (preferably stirring vigorously until the solution gradually turns from yellow to light gray, stopping stirring and ultrasonically dispersing, and washing the Ag—$Fe_3O_4$ microspheres with pure water until neutral);

(2) adding the Ag—$Fe_3O_4$ microsphere obtained in step (1) to polyetherimide (PEI, Mw¼ molecular weight 25 kDa) and basic amino acid poly-D-lysine, and reacting to obtain Ag—$Fe_3O_4$ microsphere modified with poly-D-lysine; and (3) mixing the microsphere obtained in step (2) with S100β antibody and/or MBP antibody, and adding the cross-linking agent EDC and/or NHS to promote the coupling of polylysine and the antibody by an amide bond to prepare an Ag—$Fe_3O_4$ immunomagnetic microsphere (where preferably the molar ratio of EDC:NHS is 2:1).

In step (1), the $Fe^{2+}$ and $Fe^{3+}$ metal salts are soluble salts, such as $FeCl_3$ and $FeCl_2$. Preferably, in step (1), the weight ratio of $Ag^+:Fe^{3+}:Fe^{2+}$ is 1.0:2.5:1.0.

Preferably, the concentration of triethanolamine in step (1) is 1 mol/L.

The research results of the present invention show that when the weight ratio of $Ag^+/Fe^{3+}/Fe^{2+}$ is controlled to 1.0:2.5:1.0 and the concentration of triethanolamine is 1 mol/L, the formed $Ag$—$Fe_3O_4$ magnetic microsphere has the optimum specificity for adsorbing exosomes.

Preferably, the weight ratio of $Ag$—$Fe_3O_4$ microsphere: poly-D-lysine in step (2) is 3:2-16, and preferably 3:8.

The surface of $Ag$—$Fe_3O_4$ magnetic microsphere is modified with the basic amino acid poly-D-lysine. The results show that when the weight ratio of $Ag$—$Fe_3O_4$ microsphere: poly-D-lysine is 3:8, the modified microsphere has the optimum adsorption efficiency for exosomes.

Preferably, in step (3), the weight ratio of the microsphere obtained in the step (2) to the S100β and MBP antibody is 10:1:1.

Another object of the present invention is to provide use of the $Ag$—$Fe_3O_4$ immunomagnetic microsphere according to the present invention in the extraction of nerve tissue-derived exosomes.

Another object of the present invention is to provide a method for extracting nerve tissue-derived exosomes, which comprises digesting the peripheral nerve tissue with an enzymatic digestion solution, and extracting with the $Ag$—$Fe_3O_4$ immunomagnetic microsphere of the present invention.

Preferably, the digestion solution contains DNase I, papain, hyaluronidase, collagenase I, collagenase II, and collagenase IV. More preferably, the digestion solution contains 0.05 mg/ml DNase I, 0.2 mg/ml papain, 0.1 mg/ml hyaluronidase, 1 mg/ml collagenase I, 1 mg/ml collagenase II, and 1 mg/ml collagenase IV.

The specific steps are as follows.

The peripheral nerve tissue is cut into pieces with a size of 1-2 mm³, an appropriate amount of a digestion solution (the optimal concentrations of various enzymes in D-Hank's solution: 0.05 mg/ml DNase I, 0.2 mg/ml papain, 0.1 mg/ml hyaluronidase, 1 mg/ml collagenase I, 1 mg/ml collagenase II, and 1 mg/ml collagenase IV), and incubated at 37° C. for 3 hrs. The system is diluted with a large amount of D-Hank's solution and centrifuged to remove residual enzymes. The pellet is resuspended in 10 mL of 0.01M PBS, and filtered through a 0.22 μm filter. 500 μg of $Ag$—$Fe_3O_4$ magnetic microsphere modified with poly-D-lysine and linked with S100β and MBP antibody is added to extract exocrines derived from peripheral nerve tissue.

Advantages of the Present Invention

In the present invention, $Ag$—$Fe_3O_4$ microsphere modified with poly-D-lysine and linked with S100β and MBP antibody is used to extract exocrines in peripheral nerve tissue. Compared with the traditional ultracentrifugation method, the present invention has the characteristics of high yield of exosomes per unit volume of peripheral nerve tissue and high nerve specificity, thus being suitable for extracting exosomes from peripheral nerve tissues.

BRIEF DESCRIPTION OF THE DRAWINGS

FIGS. 2B and 2C are histograms of exosome-specific proteins CD63 and HSP70.

FIG. 3B is a statistical graph of microsphere diameter).

FIG. 4B is a statistical graph of exosome diameter distribution).

DETAILED DESCRIPTION

Figure 1:
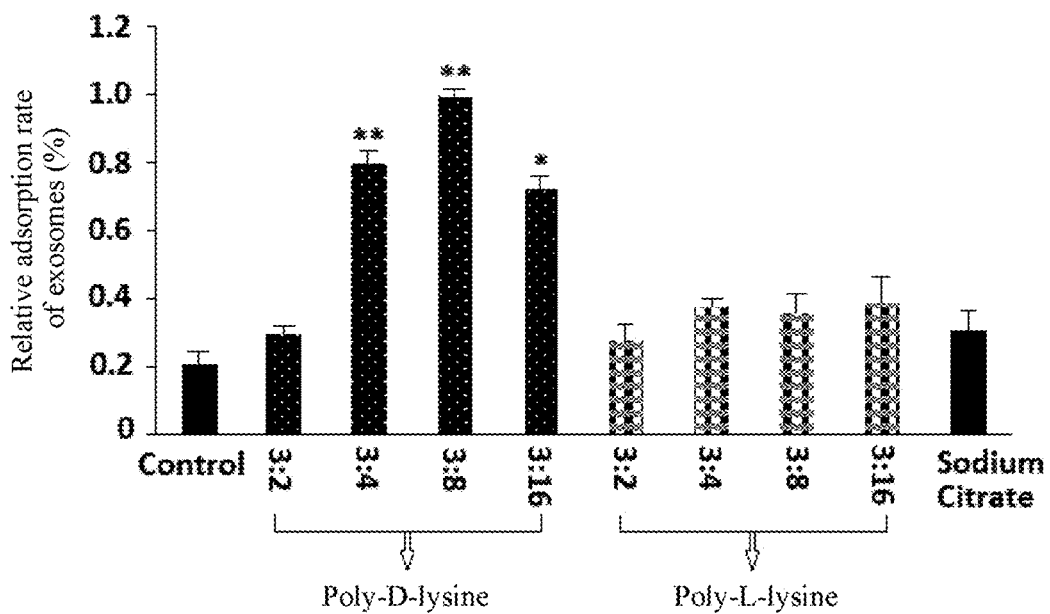
FIG. 1 shows the adsorption rates for exosomes of $Ag$—$Fe_3O_4$ microspheres modified with different types and weight ratios of polylysine.

The specific steps of the present invention are described by the following examples, but are not limited to the examples.

The terms used in the present invention, unless otherwise stated, generally have the meanings commonly understood by those of ordinary skill in the art.

The present invention is further described below in detail with reference to specific examples and relevant data. It should be understood that the examples are only used to exemplify the present invention, but do not limit the scope of the present invention in any manner.

In the following examples, various processes and methods that are not described in detail are conventional methods known in the art.

The present invention is further described below with reference to specific examples, but the protection scope of the present invention is not limited to this.

Example 1: Preparation of $Ag$—$Fe_3O_4$ Magnetic Microsphere with Silver Ions by Microemulsion Method 3 g of $FeCl_3 \cdot 6H_2O$ and 1.2 g of $FeCl_2 \cdot 4H_2O$ were respectively weighed, and dissolved in 250 mL beakers containing various concentrations of triethanolamine ($C_6H_{15}O_3N$) solution (0.16, 0.40, 1.00, and 2.50 mol/L). The contents were fully dissolved by ultrasonication at room temperature to obtain a homogeneous orange-yellow solution. Then, an aqueous silver nitrate solution was added to the $Fe^{2+}$ and $Fe^{3+}$ solution in a water bath at 75° C., under a high-purity nitrogen atmosphere, where the weight ratio of $Ag^+/Fe^{3+}/Fe^{2+}$ was controlled to 1.0:2.5:1.0. The solution was vigorously stirred for 90 min in a magnetic field (E=200 mT), and the solution gradually turned light gray. The magnetic microsphere has regular morphology and monodispersed particle size at pH=10-11. After the stirring was stopped, the solution was dispersed ultrasonically for 30 min, and the microsphere was washed with $ddH_2O$ until the pH was neutral, and then dried at 60° C. under vacuum to prepare an $Ag$—$Fe_3O_4$ microsphere.

The adsorption rates for nucleic acids and exosomes of $Ag$—$Fe_3O_4$ microspheres prepared with different concentrations of $C_6H_{15}O_3N$ were investigated (Table 1).

Commercially available calf thymus DNA (CT-DNA) and exosomes from healthy human serum were used as standards in the detection of adsorption rates for DNA and exosomes. The calf thymus DNA powder (Solarbio, Cat. No. D8020) was dissolved in 0.01M PBS to prepare a 1 mg/ml calf thymus DNA solution. The solution was stirred gently at room temperature for 1 hr to fully mix the $Ag-Fe_3O_4$ microsphere with the DNA in the solution. The DNA concentration in the solution was calculated from the net absorbance at $OD_{260}$ of the solution detected before and after the adsorption by an UV spectrophotometer, to calculate the adsorption rate for DNA of the microsphere prepared with different concentrations of $C_6H_{15}O_3N$. Powdered exosomes from healthy human serum (Rengenbio, Cat. No. EXOLyoS-2) was dissolved in 0.01M PBS to prepare a $10^{12}$/mL exosome suspension. The exosome counts in the solution before and after adsorption were calculated by NTA, to calculate the adsorption rate for exosomes of the microsphere prepared with different concentrations of $C_6H_{15}O_3N$. Results are as shown in Table 1. The results show that the microsphere prepared with 1 mol/L $C_6H_{15}O_3N$ has the highest adsorption rate for exosomes, reaching 86.42±5.84%, but has a relatively low adsorption rate for DNA (*$P<0.05$ VS. 0.16M $C_6H_{15}O_3N$ group; ##$P<0.01$ VS. 0.16M $C_6H_{15}O_3N$ group). Therefore, the $Ag-Fe_3O_4$ microsphere prepared with 1 mol/L $C_6H_{15}O_3N$ has the best specificity for adsorbing exosomes.

TABLE 1

Adsorption rates for DNA and exosomes of $Ag-Fe_3O_4$ microspheres prepared with different concentrations of $C_6H_{15}O_3N$

| $C_6H_{15}O_3N$ (M) | Absorption rate of DNAs (%) | Absorption rate of exosomes (%) |
| --- | --- | --- |
| 0.16 | 18.12 ± 2.52 | 26.75 ± 2.51 |
| 0.40 | 64.57 ± 3.47* | 61.92 ± 4.03 |
| 1.00 | 25.37 ± 3.85 | 86.42 ± 5.84## |
| 2.50 | 19.65 ± 2.12 | 35.46 ± 6.22 |

Example 2: Preparation of Magnetic Microsphere Modified with Poly-D-Lysine $Ag-Fe_3O_4$ microsphere prepared with 1 mol/L $C_6H_{15}O_3N$ in Example 1 was added with polyetherimide (PEI, Mw % molecular weight 25 kDa), and modified by reaction with the basic amino acid poly-D-lysine and poly-L-lysine, where the weight ratio of $Ag-Fe_3O_4$ microsphere: PEI:polylysine was 3:1:2, 3:1:4, 3:1:8, and 3:1:16 respectively. Sodium citrate modified microsphere was used as a control (Stem cell-mediated delivery of nanogels loaded with ultrasmall iron oxide nanoparticles for enhanced tumor MR imaging, *Nanoscale*. 2019 Mar. 14; 11(11):4904-4910). The unmodified $Ag-Fe_3O_4$ microsphere was used as a blank control.

FIG. 1 shows the adsorption rates for exosomes of microspheres modified with different types and weight ratios of polylysine. The results show that $Ag-Fe_3O_4$ microsphere modified with poly-D-lysine can significantly improve the adsorption for exosomes by $Ag-Fe_3O_4$ microsphere compared with the $Ag-Fe_3O_4$ microsphere modified with poly-L-lysine. Moreover, the $Ag-Fe_3O_4$ microsphere modified with poly-D-lysine has the best adsorption efficiency for exosomes when prepared at a weight ratio of $Ag-Fe_3O_4$ microsphere:polylysine of 3:8 (*$P<0.05$, **$P<0.01$ VS. Control).

Example 3: Preparation of Specific Immunomagnetic Microsphere

The commercially available S100β antibody (50 μg, Proteintech, cat. No. 15146-1-AP or MBP antibody (50 μg, R&D company, cat. No. MAB42282 were mixed with 1 mg, 500 μg, or 250 μg of $Ag-Fe_3O_4$ microsphere modified with poly-D-lysine prepared under the optimal conditions in Example 2. A mixed solution of 1.0M EDC and 0.5M NHS was added to promote the covalent coupling between carboxyl/amino groups of polylysine and the antibody, to prepare $Ag-Fe_3O_4$ immunomagnetic microsphere.

Powdered exosomes from healthy human serum (Rengenbio, Cat. No. EXOLyoS-2) was dissolved in 0.01M PBS to prepare a 1 mg/ml exosome suspension. 1 mg of the microsphere prepared with different weight ratios of poly-D-lysine modified $Ag-Fe_3O_4$ microsphere and antibody was respectively added to an exosome suspension to adsorb the exosomes in the solution. The expression level of exosome specific marker adsorbed by the immunomagnetic microsphere was determined by Western blot, to determine the adsorption efficiency for exosomes of the immunomagnetic microsphere prepared with different weight ratios of microsphere/antibody.

The immunomagnetic microsphere adsorbed with the exosomes was collected in an external magnetic field. A protein lysis buffer and a protease inhibitor were added and the total protein were detected. The expression levels of the exosome specific markers CD63 and HSP70 were determined by Western blot. The extracted total protein was dissolved in 2×SDS loading buffer, and boiled for 5 min. 10 g of the supernatant was subjected to 10% SDS-PAGE electrophoresis. After the electrophoresis, the sample was transferred to a PVDF membrane (40 mA, 2 hrs). After that, the membrane was rinsed with 25 mL of TBS/T for 5 min at room temperature, and then the PVDF membrane was placed in TBS/T containing 5% skimmed milk powder and coated overnight at 4° C. The membrane was rinsed with TBS/T (5 min×3), and the primary antibodies monoclonal antibody mouse anti-CD63 (1:1000 dilution, Abcam, ab108950) and monoclonal antibody rabbit anti-HSP70 (1:1000 dilution, Abcam, ab181606) were added and incubated at 4° C. overnight. The membrane was rinsed with TBS/T (5 min×3), and the secondary antibodies HRP-conjugated goat anti-mouse IgG (1:2000 dilution) and HRP-conjugated goat anti-rabbit IgG (1:2000 dilution) were added and incubated for 2 hrs at room temperature. The membrane was rinsed with TBS/T (5 min×3), placed in an ECL developing solution (each 300 μl of A and B, mixed well before use), and stood at room temperature for 2 min. The membrane was filmed, exposed, and developed. A blank control group without primary antibody was set in the experiment. For the blank control group, the steps were the same as above except that the primary antibody was replaced by 0.01M PBS. The experiment was triplicated. GAPDH (1:4000) was used as an internal reference. The image was scanned in grayscale with GS800 Calibrated Densitometer scanner, and the results were analyzed by PDQuest 7.2.0 software.

Figure 2:
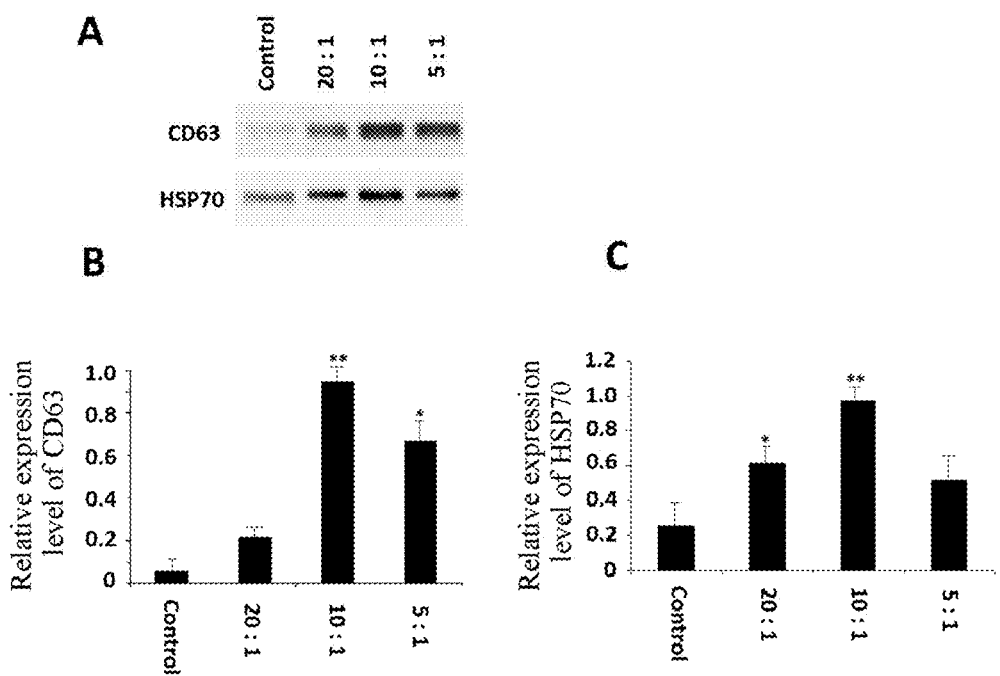
FIG. 2 shows exosome-specific proteins adsorbed by immunomagnetic microspheres prepared with different ratios of poly-D-lysine modified $Ag$—$Fe_3O_4$ microsphere and antibody (FIG. 2A is a representative western blot of exosome-specific proteins CD63 and HSP70.

FIG. 2 shows a representative western blot (FIG. 2A) and a histogram (FIG. 2B) of exosome-specific proteins CD63 and HSP70 adsorbed by immunomagnetic microspheres prepared with different ratios of poly-D-lysine modified Ag—Fe$_3$O$_4$ microsphere and antibody. The results show that there is statistical difference for exosome-specific protein CD63 when the ratio of poly-D-lysine modified Ag—Fe$_3$O$_4$ microsphere to the antibody is 10:1 and 5:1 (*P<0.05, **P<0.01 VS. Control). The result is the most desirable when the ratio is 10:1. There is statistical difference for exosome-specific protein HSP70 when the ratio of poly-D-lysine modified Ag—Fe$_3$O$_4$ microsphere to the antibody is 20:1 and 10:1 (*P<0.05, **P<0.01 VS. Control). The result is the most desirable when the ratio is 10:1. Therefore, a specific immunomagnetic microsphere was prepared at a most preferred ratio of poly-D-lysine modified Ag—Fe$_3$O$_4$ microsphere to S100β antibody and MBP antibody of 10:1:1.

Figure 3:
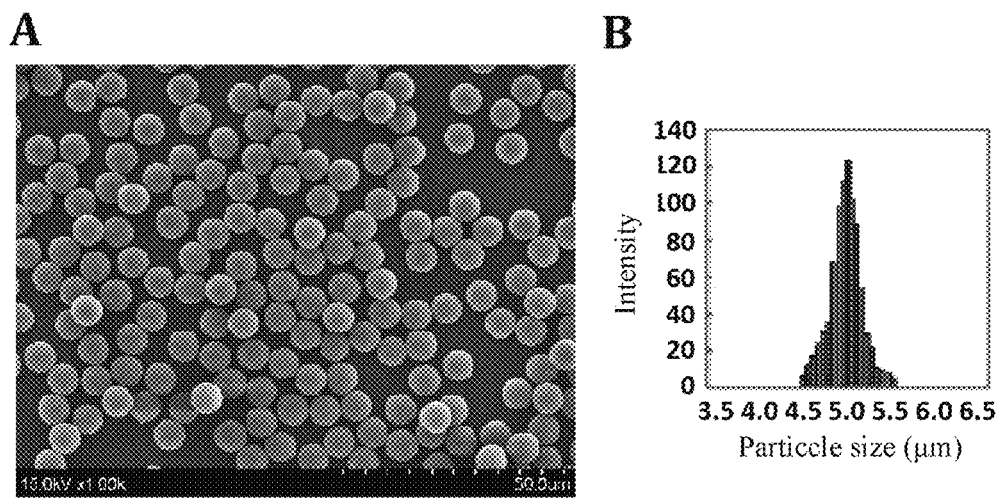
FIG. 3 shows a scanning electron microscopy (SEM) image of $Ag$—$Fe_3O_4$ immunomagnetic microsphere and a statistical graph of microsphere diameter (FIG. 3A is a representative SEM image of magnetic microspheres.

The immunomagnetic microsphere prepared under optimal conditions was observed by scanning electron microscopy, and the diameter range and distribution of the microsphere was statistically calculated. The image resolution is 1 k, when a cold field emission scanning electron microscope (JEM-T300, JEOL Inc., Japan) and a secondary electron detector are used. FIG. 3 shows an SEM image of the magnetic nano-microsphere and a statistical graph of microsphere diameter. The results show that as observed under a scanning electron microscope, the immunomagnetic microsphere has a nearly spherical shape, a smooth and intact surface, a good dispersion, and a basically uniform size (FIG. 3A) and the particle size is mainly distributed in the range of 4.5-5.5 μm, with an average diameter of 5 μm (FIG. 3B).

Example 4: Extraction of Peripheral Nerve Tissue-Derived Exosomes 10 g of peripheral nerve tissue was placed on ice, from which the wrapped connective tissue and epineurium were carefully removed under a dissecting microscope, and then transferred to a petri dish filled with D-Hank's solution on ice. The peripheral nerve tissue was cut into tissue pieces of about 1 mm$^3$ by microsurgical scissors, added with 20 mL of a tissue digestion solution (where the final concentrations of various enzymes were 0.05 mg/ml DNase I, 0.2 mg/ml papain, 0.1 mg/ml hyaluronidase, 1 mg/ml collagenase I, 1 mg/ml collagenase II, and 1 mg/ml collagenase IV in D-Hank's solution) and incubated at 37° C. for 3 hrs. After dilution with a large amount of D-Hank's solution, the solution was centrifuged to remove residual enzymes. The pellet was resuspended in 10 mL of 0.01M PBS, and filtered through a 0.22 μm filter. 1 mg of the immunomagnetic microsphere prepared at a most preferred ratio of poly-D-lysine modified Ag—Fe$_3$O$_4$ microsphere to S100β antibody and MBP antibody of 10:1:1 in Example 3 was added, swirled and mixed thoroughly, and then rotated and mixed overnight at 4° C. for >16 hrs. Solid-liquid separation was performed in an external magnetic field, and the supernatant was discarded to obtain a poly-D-lysine-modified Ag—Fe$_3$O$_4$-S100β/MBP antibody-exosome complex. The product was resuspended in 0.01M PBS, and subjected to solid-liquid separation in an external magnetic field to remove cell debris and other impurities. Then the microsphere complex precipitated at the bottom of the tube was fully dissolved in a glycine solution (pH=3) with a concentration of 0.2 mol/L, to dissociate the antibody from the exosomes, and then neutralized with a 0.1 mol/L Tris solution (pH=10) and adjusted to a suitable pH. Solid-liquid separation was performed in an external magnetic field, the precipitated microsphere was discarded, and the supernatant was collected. The extracted peripheral nerve tissue-derived exosomes were present in the supernatant. The supernatant was centrifuged at 4° C. and 1500 g for 30 min. Then the pellet was resuspended in 100 μl of 0.01M PBS, to obtain a solution of nerve tissue-derived exosomes.

Figure 4:
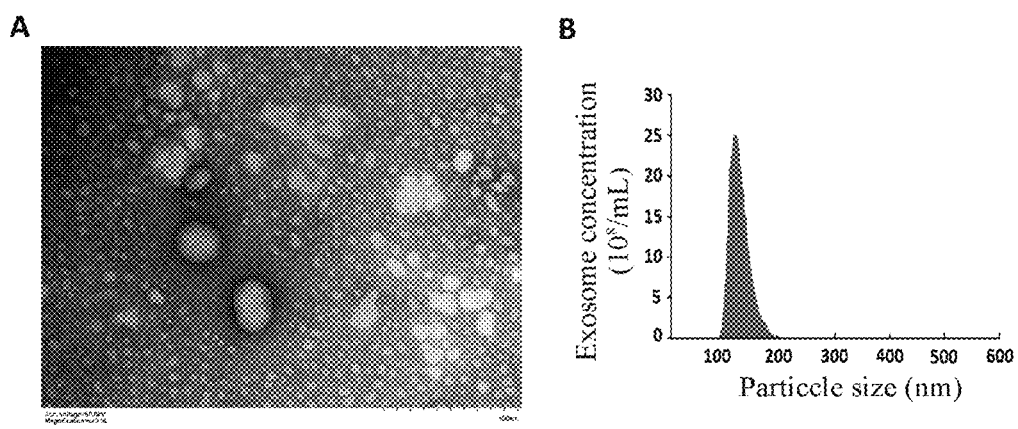
FIG. 4 shows a transmission electron microscopy (TEM) image of exosomes and a statistical graph of diameter by NTA (FIG. 4A is a representative TEM image of exosomes.

The concentration and size distribution of exosomes particles were detected by nanoparticle tracking analysis (NTA), and analyzed b ZataView 8.04.02 software. FIG. 4 is a TEM image showing the size and morphology of exosomes. FIG. 4A is a TEM image of the exosomes extracted by Ag—Fe$_3$O$_4$ immunomagnetic microsphere. The diameter is 30-150 nm, and the capsule-like ultrastructure is clearly visible, which is consistent with the morphological characteristics of exosomes. From the statistical analysis of particle size in FIG. 4B, the average particle size is 120 nm.

Figure 5:
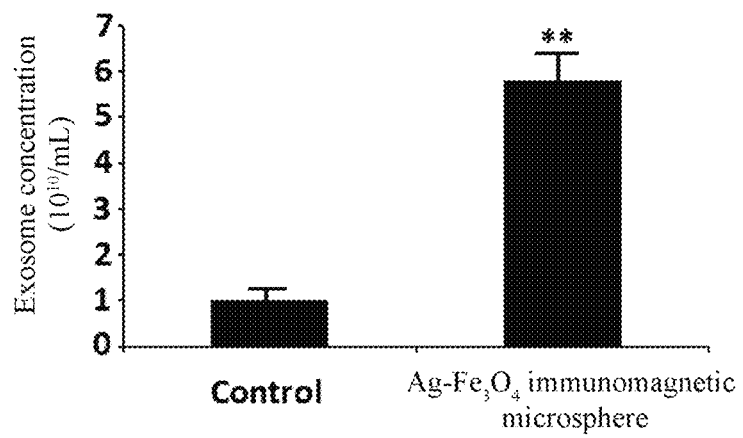
FIG. 5 shows the effect of $Ag$—$Fe_3O_4$ immunomagnetic microsphere and traditional ultracentrifugation in extracting exosomes as detected by NTA.

Following the method disclosed in A protocol for exosome isolation and characterization: evaluation of ultracentrifugation, density-gradient separation, and immunoaffinity capture methods, *Methods Mol Biol.* 2015; 1295:179-209, the exosomes extracted by the traditional ultracentrifugation method are compared with those obtained by the extraction method of the present invention. The concentration of exosomal particles was detected by NTA. The prepared exosome suspension was diluted 1000 times with 0.01M PBS, the instrument was calibrated with polystyrene particles with a diameter of 100 nm, and the sample pool was washed with ultrapure water. At room temperature, the exosome suspension samples were loaded, the concentration of exosomes particles was detected by the ZataView 8.04.02 software, and the analysis results was statistically calculated by SPSS 11.5. FIG. 5 is a histogram of the concentration detected by NTA of exosomes obtained by different extraction methods. The concentrations of exosomes extracted by the Ag—Fe$_3$O$_4$ immunomagnetic microsphere of the present invention and by traditional ultracentrifugation in the control group are compared, and the results show a significant difference (**p<0.01 VS. Control), indicating that the exosomes extracted by the Ag—Fe$_3$O$_4$ immunomagnetic microsphere have the characteristics of high yield of exosomes per unit volume of peripheral nerve tissue.

Example 5: Effect of Exosomes Obtained by Different Extraction Methods on the Specific Differentiation of Embryonic Stem Cells into Neuron-Like Cells Preparation of feeder cells, namely primary mouse embryo fibroblast (PMEF): Mouse embryos of 13.5 d were stood in ice-cold D-Hank's solution, and the torso was cut into pieces of 1 mm$^3$, digested with 0.25% trypsin at 37° C. for 10 min, and then quenched with serum. Then, the cells were cultured in a plate in PMEF growth medium (high-glucose DMEM, containing 0.1 mmol/L β-ME and 10% fetal bovine serum) at a density of 5×10$^5$/mL. After the PMEFs were sub-cultured to the third generation, 10 mg/L mitomycin C was added, and co-incubated for 2 hrs. Then, the cells were used as the feeder layer cells after thorough washing.

ES-D3 embryonic stem cells were seeded on the feeder cells at a certain density in high-glucose DMEM containing 0.1 mmol/L β-ME, 1% non-essential amino acids, 10$^6$ U/L LIF and 10% FBS, and generally sub-cultured once every 2-3 days. When the cells were grown to nearly 80% confluence, they were digested with trypsin to form a single cell suspension. The ES cells were re-seeded in a differentiation medium I (high-glucose DMEM containing non-essential amino acids and 10% fetal calf serum, without LIF) in a 6-well plate without feeder layer, and the medium was gradually replaced by a serum-free PMEF growth medium in which different concentrations of exosomes obtained by different extraction methods were added (exosomes obtained by the method of the present invention in Example 4 and exosomes obtained by the traditional ultracentrifugation method). After another 3 days of culture, the cells were immunocytochemically stained to observe the percentage of embryonic stem cells differentiated into Tuj1-positive neuron-like cells.

The cells were immobilized in 4% paraformaldehyde at room temperature for 15 min, and washed with 0.01M PBS (10 min×3). The plate was blocked with 0.01M PBS containing 10% goat serum and 0.3% Triton X-100 for 60 min. Fluorescence immunocytochemical analysis: The primary antibody (rabbit anti-Tuj1 polyclonal antibody, 1:350) was dripped, stood overnight at 4° C., and washed with 0.01M PBS for 10 min (×3). The secondary antibody (FITC donkey anti-rabbit IgG, 1:1000) was dripped, and the cell nucleus was labeled with Hoechst33342 (5 μg/ml), stood at room temperature for 1 hr in the dark. The cells were then washed with 0.01M PBS (10 min×3). A blank control group without primary antibody was set in the experiment. Under a laser confocal microscope (FITC excitation wavelength: 488 nm, observation wavelength: 500-535 nm; Hoechst33342 argon-ion Ar excitation wavelength: 353-364 nm, observation wavelength: 460-480 nm), the results of fluorescence immunocytochemical detection were observed. The percentage of Tuj1 positive cells and the total axon length were statistically calculated by ImageJ software.

The statistical results of fluorescence immunocytochemical staining in Table 2 show that compared with the percentage of Tuj1 positive cells and the total axon length in the negative control group treated only with the neuronal medium 97% Neurobasal+2% B27+1% GluMAX, at an exosome concentration of $10^7$/mL extracted by Ag—$Fe_3O_4$ immunomagnetic microsphere, the percentage of Tuj1 positive cells is 0.38±0.11, and the total axon length is 15.34±1.64 μm (*p<0.05 VS. Control; #p<0.05 VS. exosomes concentration $10^8$/mL by ultracentrifugation). At an exosome concentration of $10^8$/mL extracted by Ag—$Fe_3O_4$ immunomagnetic microsphere, the percentage of Tuj1 positive cells is 0.88±0.09, and the total axon length is 31.89±2.09 μm (**p<0.01 VS. Control; ##p<0.01 VS. exosomes concentration $10^8$/mL by ultracentrifugation). There are significant differences. The situation is most preferred where the exosome concentration extracted by Ag—$Fe_3O_4$ immunomagnetic microsphere is $10^8$/mL. This shows that with the addition of different concentration gradients of exosomes is positively correlated with the percentage of stem cells that differentiate into neuron-like cells, suggesting that the exosomes extracted by Ag—$Fe_3O_4$ immunomagnetic microsphere of the present invention have specificity for promoting differentiation of embryonic stem cells into neuron-like cells, and this specificity is higher than that of exosomes obtained by ultracentrifugation.

TABLE 2

Effect of different concentrations of exosomes extracted by Ag—$Fe_3O_4$ immunomagnetic microsphere on the differentiation of stem cells into neuron-like cells

| Experiment group | Percentage of Tuj1 positive cell (%) | Total axon length (μm) |
|---|---|---|
| Control | 0.09 ± 0.03 | 1.50 ± 0.12 |
| Exosome concentration $10^5$/mL extracted by the present method | 0.12 ± 0.02 | 2.65 ± 0.74 |
| Exosome concentration $10^6$/mL extracted by the present method | 0.22 ± 0.05 | 4.32 ± 1.24 |
| Exosome concentration $10^7$/mL extracted by the present method | 0.38 ± 0.11* | 15.34 ± 1.64*,# |
| Exosome concentration $10^8$/mL extracted by the present method | 0.88 ± 0.09**,## | 31.89 ± 2.09**,## |
| Exosome concentration $10^8$/mL extracted by ultracentrifugation | 0.22 ± 0.10 | 2.53 ± 1.08 |

The invention claimed is:

1. An Ag—$Fe_3O_4$ immunomagnetic microsphere, comprising a surface modified with poly-D-lysine and S100β antibody and/or MBP antibody linked to the poly-D-lysine by an amide bond.

2. A method for preparing the Ag—$Fe_3O_4$ immunomagnetic microsphere according to claim 1, comprising:
   (1) dissolving a $Fe^{2+}$ salt and a $Fe^{3+}$ metal salt in an aqueous triethanolamine solution, heating the aqueous triethanolamine solution, adding an aqueous $Ag^+$ solution under an inert gas atmosphere into the heated aqueous triethanolamine solution to obtain Ag—$Fe_3O_4$ microsphere, and washing the obtained Ag—$Fe_3O_4$ microsphere;
   (2) adding the Ag—$Fe_3O_4$ microsphere obtained in step (1) to polyetherimide and poly-D-lysine, and reacting to obtain Ag—$Fe_3O_4$ microsphere modified with poly-D-lysine; and
   (3) mixing the Ag—$Fe_3O_4$ microsphere modified with poly-D-lysine obtained in step (2) with an antibody that is S100β antibody, MBP antibody, or a mixture thereof, and adding a cross-linking agent EDC and/or NHS to promote linking of poly-D-lysine and the antibody by an amide bond to prepare the Ag—$Fe_3O_4$ immunomagnetic microsphere.

3. The method according to claim 2, wherein a weight ratio of $Ag^+$:$Fe^{3+}$:$Fe^{2+}$ in step (1) is 1.0:2.5:1.0.

4. The method according to claim 2, wherein a concentration of triethanolamine in step (1) is 1 mol/L.

5. The method according to claim 2, wherein a weight ratio of Ag—$Fe_3O_4$ microsphere:poly-D-lysine in step (2) is 3: 2-16.

6. The method according to claim 2, wherein in step (3), a weight ratio of the microsphere obtained in step (2) to the S100β or MBP antibody is 10:1.

7. A method for extracting nerve tissue-derived exosomes, comprising digesting a peripheral nerve tissue with an enzymatic digestion solution to form a digestion solution, and extracting the digestion solution with the Ag—$Fe_3O_4$ immunomagnetic microsphere according to claim 1.

8. The method according to claim 7, wherein the digestion solution comprises DNase I, papain, hyaluronidase, collagenase I, collagenase II, and collagenase IV.

9. The method according to claim 7, wherein the digestion solution comprises 0.05 mg/ml DNase I, 0.2 mg/ml papain, 0.1 mg/ml hyaluronidase, 1 mg/ml collagenase I, 1 mg/ml collagenase II, and 1 mg/ml collagenase IV.

* * * * *